United States Patent [19]

Rauschenberger

[11] 4,160,383
[45] Jul. 10, 1979

[54] UNITARY SAMPLE-VENT-VALVE ASSEMBLY

[75] Inventor: Richard A. Rauschenberger, Brookfield, Wis.

[73] Assignee: Will Ross Inc., Milwaukee, Wis.

[21] Appl. No.: 864,580

[22] Filed: Dec. 27, 1977

[51] Int. Cl.² .................. G01N 1/20; A61F 5/44
[52] U.S. Cl. .................. 73/422 R; 128/274; 128/295; 137/588; 137/855
[58] Field of Search ............ 73/422 R, 425; 128/295, 128/274, DIG. 24, 2 F; 137/588, 587, 855

[56] References Cited

U.S. PATENT DOCUMENTS

| 2,722,896 | 11/1955 | Hayes | 137/855 |
| 2,867,213 | 1/1959 | Thomas | 128/274 |
| 3,830,241 | 8/1974 | Dye | 128/274 |
| 3,901,235 | 8/1975 | Patel | 137/855 |
| 3,906,935 | 9/1975 | Raia | 128/295 |
| 3,908,656 | 9/1975 | Binard | 128/295 |
| 4,013,064 | 3/1977 | Patel | 128/295 |

Primary Examiner—S. Clement Swisher
Assistant Examiner—Denis E. Corr
Attorney, Agent, or Firm—John A. Dhuey

[57] ABSTRACT

A unitary sample-vent-valve assembly, useful in urological applications, is described. The unitary assembly comprises a sequential arrangement of valve, vent and sampling port to afford a compact unit.

5 Claims, 4 Drawing Figures

UNITARY SAMPLE-VENT-VALVE ASSEMBLY

The invention is concerned generally with devices useful in urological applications. More particularly, it is concerned with a unitary assembly having a sequential arrangement of valve, vent and sample port for use in fluid drainage lines connected to fluid collection containers.

The invention will be described with reference to the following drawings in which.

Figure 1:
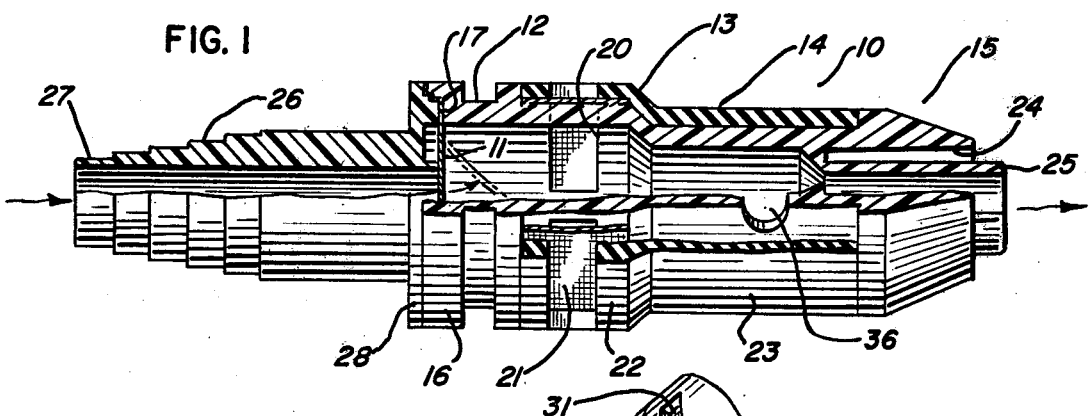
FIG. 1 is an elevational view of one embodiment of the invention, partially in section.
Figure 3:
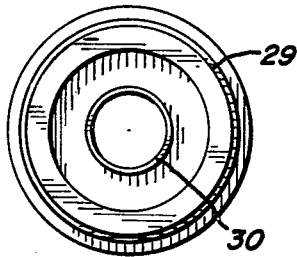
FIG. 3 is an end view of the tubing connector.
Figure 2:
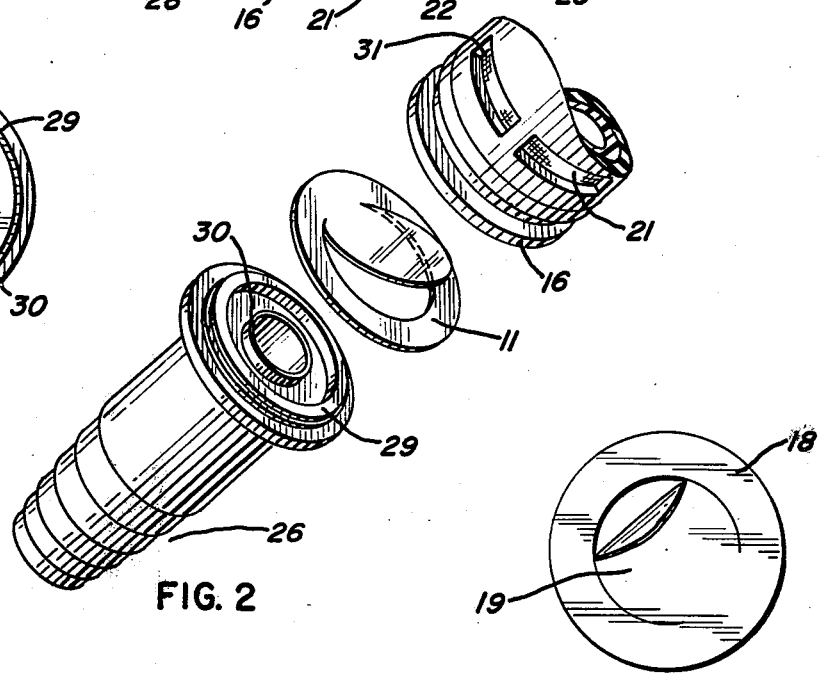
FIG. 2 is an exploded view of the valve and tubing connector.
Figure 4:
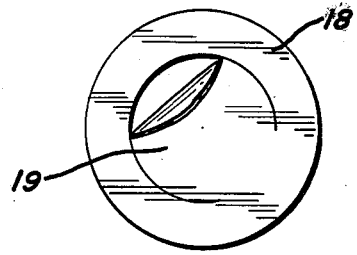
FIG. 4 is a top view of the valve disc.

With reference to the drawings, the unitary valve-vent-sample assembly comprises a tubular body 10 having a first end 12, a first intermediate section 13 adjacent first end 12 and a second intermediate section 14 adjacent a second end 15. First end 12 is formed with a flange 16 having a circumferential recess 17 formed therein. Recess 17 is adapted to receive and support a valve means 11.

Valve means 11 preferably is a disc shaped member comprising a main body portion 18 having a C-shaped flap 19 formed therein. A polyester material (MYLAR ®) has been found to be eminently suitable for the manufacture of valve 11.

First intermediate section 13 defines vent openings 20 and supports venting means 21. Venting means 21 is ring-shaped and formed from a semipermeable fabric which surrounds section 13, overlaying openings 20. The fabric is permeable to air but not to liquid. Particularly suitable for that purpose is a polytetrafluoroethylene fabric having interconnected pores of about 0.45 microns. The fabric ring is slipped over intermediate section 13 and held in place by retainer 22 which defines openings 31 corresponding to openings 20. In an alternate embodiment, the vent material can be bonded to the inner surface of intermediate section 13 at a position to overlay vent openings 20.

Second intermediate section 14 defines a sample port 36 in the wall of body 10 and is encompassed by a flexible member 23, which is adapted to be pierced by a syringe needle to obtain fluid samples and is resealable upon removal of the needle. A raised demarcation point is placed in the outer surface of member 23 over sample port 36 to assist in needle placement. A latex sleeve can be employed for member 23. However, it has been found preferable to replace the conventional latex sleeve with a sleeve of thermoplastic rubber. It is even more preferable to form members 22 and 23 as a unitary structure from thermoplastic rubber (e.g. KRATON ®). The unitary structure then functions to retain the vent material on section 13 and form the resealable covering on section 14. This method of construction is particularly advantageous where the polytetrafluoroethylene material is used as vent material since it is difficult to bond to other surfaces.

End section 15 is provided with an inner surface 24 and an inner tubular member 25, which preferably extends past the end of surface 24. The space defined by surface 24 and the outside of tubular member 25 receives accessory tubing such that the tubing wall surrounds member 25. Such an arrangement provides a tight fit even in the presence of minor variations in accessory tubing diameter.

A tube connector cap 26 is provided for attachment at the first end of assembly 10 and attachment to drainage tubing from a patient. Cap 26 terminates in a graduated tubing connector end 27 and flange 28. Raised rib 29 on flange 28 cooperates with recess 17 on flange 16 and is effective to retain valve 11 therein and align cap 26 with tubular body 10. Rib 30 is concentric with and of lesser diameter than rib 29 and provides a seat for valve 11. Cap 26 preferably is made opaque so that the normal fluid column above the valve cannot be seen. That fluid column is normal with small bore catheters since no air can exchange. A novice might infer from the sight of the fluid column that the valve is not working correctly and take unnecessary action. When cap 26 is opaque, this potential problem is not present.

Tubular body 10 is molded in a single, conventional operation to include vent holes 20 and sample port 36. Then ring 21 is slipped over intermediate portion 13 and a second molding operation is performed to fabricate retention and sample sleeve 22 and 23. The overmolding operation provides a unitary structure for members 22 and 23. Finally, the polyester valve 11 is placed on the end of the tubular housing and tube connector cap 26 is ultrasonically bonded to body 10. Disc 11 is effectively retained therebetween.

The instant invention presents numerous advantages over prior art systems. In particular, positioning the vent portion of the assembly between the valve and the drainage bag permits the drainage line and the bag to be vented without having a separate vent in the body of the bag. Additionally, positioning of the sample port after the valve facilitates sampling from low fluid-output patients.

The invention has been described with reference to the drawings. However, they are illustrations of the preferred embodiments of the invention and not intended to limit the invention either in spirit or in scope.

What is claimed is:

1. A unitary sample-vent-valve assembly comprising:
   a tubing connector having a first end and a second end, said first end being adapted for attachment to accessory patient tubing and said second end terminating in a first flange having first and second concentric ribs on the face thereof, said second rib being of greater diameter than said first rib;
   a tubular body having a second flange at one end thereof joined to said tubing connector and adapted to engage a fluid line at the other end thereof, said second flange having a circular recess on its face to cooperatively engage said second rib and align said tubular body with said tubing connector, said tubular body defining at least one first opening through its sidewall and a second opening through its sidewall;
   valve means retained between said first and second flanges, said first rib forming a seat for said valve means;
   vent means formed of a semi-permeable material layer overlying said first opening, and
   sampling means formed of a resealable, pierceable material overlying said second opening.

2. An assembly as in claim 1 wherein said semi-permeable layer is a continuous ring encompassing a portion of said tubular body and the first wall opening defined by said body.

3. An assembly as in claim 2 further comprising retaining means for maintaining said layer over said opening.

4. An assembly as in claim 1 wherein said valve means is a disc having a C-shaped flap adapted to seat on said first rib.

5. An assembly as in claim 1 wherein said tubular body has an inner tubular member at its second end in a spaced relationship from the wall of said body for insertion into a fluid line.

* * * * *